(12) United States Patent
Li et al.

(10) Patent No.: US 10,336,813 B2
(45) Date of Patent: *Jul. 2, 2019

(54) FUSION PROTEIN SLIT2D2-HSA AND ITS USE IN TREATMENT OF SEPSIS

(71) Applicant: Huashun Li, Suzhou (CN)

(72) Inventors: Huashun Li, Suzhou (CN); Baoyong Ren, Suzhou (CN); Ya Deng, Suzhou (CN); Rong Cheng, Suzhou (CN)

(73) Assignee: ASCLEPIUS (SUZHOU) TECHNOLOGY COMPANY GROUP CO., LTD., Suzhou (CN)

( * ) Notice: Subject to any disclaimer, the term of this patent is extended or adjusted under 35 U.S.C. 154(b) by 0 days.

This patent is subject to a terminal disclaimer.

(21) Appl. No.: 15/669,766

(22) Filed: Aug. 4, 2017

(65) Prior Publication Data

US 2018/0094045 A1    Apr. 5, 2018

Related U.S. Application Data

(63) Continuation of application No. PCT/CN2015/092079, filed on Oct. 16, 2015.

(30) Foreign Application Priority Data

Oct. 14, 2015  (CN) .......................... 2015 1 0661923

(51) Int. Cl.
| | |
|---|---|
| *A61K 38/00* | (2006.01) |
| *A61K 38/17* | (2006.01) |
| *A61P 31/04* | (2006.01) |
| *C07K 14/47* | (2006.01) |
| *C12N 15/62* | (2006.01) |
| *C07K 14/765* | (2006.01) |

(52) U.S. Cl.
CPC ............ *C07K 14/765* (2013.01); *A61K 38/17* (2013.01); *A61P 31/04* (2018.01); *C07K 14/4702* (2013.01); *C07K 14/473* (2013.01); *C12N 15/62* (2013.01); *A61K 38/00* (2013.01); *C07K 2319/31* (2013.01)

(58) Field of Classification Search
CPC ......... A61K 38/00; A61K 38/17; A61P 31/04; C07K 14/4702; C07K 14/473; C07K 14/765; C07K 2319/31; C12N 15/62
See application file for complete search history.

(56) References Cited

U.S. PATENT DOCUMENTS

| | | | |
|---|---|---|---|
| 2005/0186664 A1* | 8/2005 | Rosen ................... | A61K 38/04 435/69.7 |
| 2018/0163214 A1* | 6/2018 | Li ......................... | A61K 38/17 |

* cited by examiner

*Primary Examiner* — Marcela M Cordero Garcia
(74) *Attorney, Agent, or Firm* — Flener IP & Business Law; Zareefa B. Flener

(57) ABSTRACT

Disclosed is a fusion protein Slit2D2-HSA formed by fusion of a Slit2D2 polypeptide and a human serum albumin HSA, and use thereof for the manufacture of a medicament for prophylaxis and/or treatment of sepsis, and the said fusion protein Slit2D2-HSA retains the pharmacological activities of Slit2 in inhibition of neutrophil migration and treatment of sepsis, and has an improved stability, prolonged half-life and improved therapeutic effect of sepsis. Compared with protein of Slit2, the polypeptide of Slit2D2 has a smaller molecular weight which is much easier to be purified and separated in preparation and used in the development of drugs.

4 Claims, 4 Drawing Sheets

Specification includes a Sequence Listing.

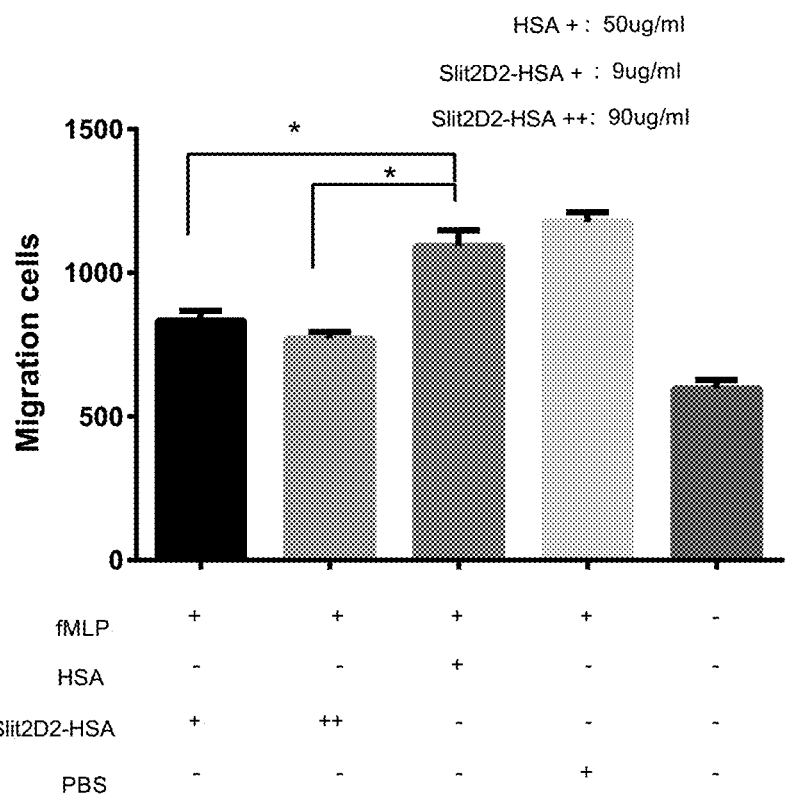
FIG. 3
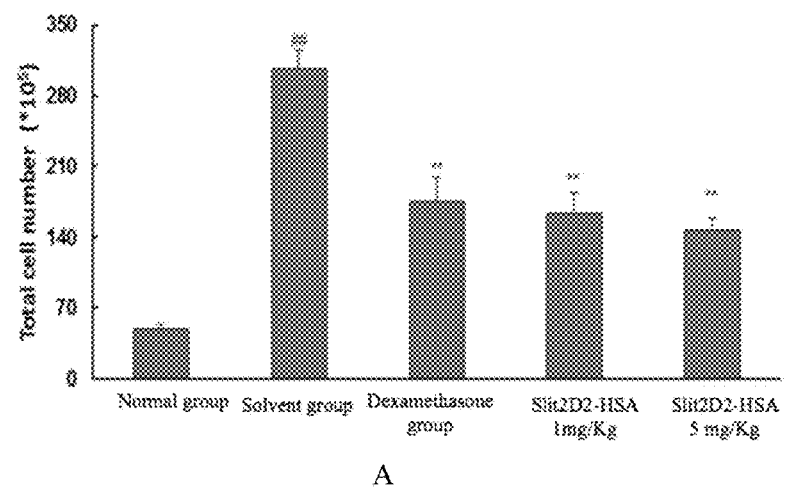
A

B

FUSION PROTEIN SLIT2D2-HSA AND ITS USE IN TREATMENT OF SEPSIS

CROSS-REFERENCE TO RELATED APPLICATION

The application is a continuation of PCT/CN2015/092079 (filed on Oct. 16, 2015), which claims priority of CN patent Application Serial No. 201510661923.6 (filed on Oct. 14, 2015), the contents of which are incorporated herein by reference in their entirety.

FIELD OF THE INVENTION

The present invention is related to the field of treatment of sepsis, particularly to use of fusion protein Slit2D2-HSA for a medicament for prophylaxis and/or treatment of sepsis.

BACKGROUND OF THE INVENTION

Sepsis refers to systemic inflammatory response syndrome (SIRS) caused by infections, and the infection sources include bacterial, fungi, viruses, parasites, etc. Sepsis often occurs in patients with severe diseases, such as severe burns, multiple traumas, and other patients after surgery. Sepsis can be divided into: sepsis, severe sepsis, and septic shock, according to the severity thereof. The incidence of sepsis is so high that there are more than 18 million cases of severe sepsis in the world, and 750,000 patients with sepsis in the United States each year, and the number is rising at an annual rate of 1.5%~8.0%. Sepsis is a serious disease with a high mortality, and there are about 14,000 deaths in worldwide caused by complications of sepsis every day, 21.5 million deaths in the United States every year. According to a foreign epidemiological investigation, the mortality of sepsis has exceeded myocardial infarction, as the main cause of death for non-cardiac intensive patients in ICU. In recent years, although the anti-infection therapy and organ support technology have made considerable progress, the mortality of sepsis is still as high as 30% to 70%. The high cost and medical resource consumption for the sepsis treatment seriously impact the quality of human life and cause a great threat to human health.

Neutrophils play a key role in the defense against infection which are quickly mobilize from the bone marrow and congregated at the sites of inflammation after infection, and used for releasing proteolytic enzymes, reactive oxygen species, cytokines and other substances to clear pathogenic microorganisms. In this process, overreaction will cause body injury, severe cases may cause tissue and organ dysfunction or decline which lead to the present of severe sepsis or septic shock.

Neuronal migration protein Slit is an evolutionarily highly conserved secreted extracelluar matrix glycoprotein with a molecular weight of about 200 kD, which plays a guiding role for axon growth and neuronal migration. The Slit gene cloned in mammals has three members, slit1, slit2 and slit3, which is composed of an extracellular signal peptide at N-terminal, four leucine-rich repeats (LRRs), also named as D1-D4 domain, a plurality of EGF (epidermal growth factor)-like repeats (seven in Drosophilidae and nine in vertebrate), a laminin G-like domain and a cysteine-rich C-terminal region, and among which Slit-2 is the most important. Robo protein family, a receptor family of Slit, is a single-channel transmembrane receptor. Slit functions by binding with the Robo receptor, and the LRRs domain is a region for the binding of Slit protein with Robo receptor. At present, there are literatures reporting that Slit2 protein may inhibit migration of neutrophils.

Recent research shows that Slit protein plays a major role in angiogenesis, tumor cell migration, leukocyte chemotaxis, etc. In U.S. Pat. No. 8,399,404B2, Slit protein and nucleic acids are used for the treatment of platelet coagulation and other related disorders, and a vascular device using Slit protein coating and cells capable of expressing a Slit protein are also disclosed. Patent WO2009105457 discloses a method and composition for cancer diagnosis, research and therapy, involving Slit2 protein, a tumor marker, effectively used as a diagnostic marker and clinical target for prostate cancer.

Tole et al., through the study, have found that the Slit2 protein inhibits the migration of neutrophils by inhibiting actin filament formation and cell polarization induced by chemokines. (The axonal repellent, Slit2, inhibits directional migration of circulating neutrophils. J Leukoc Biol. 2009, 86(6):1403-15)

Hohenester has found that Slit-Robo interaction is formed by IG1 domain of Robo binding with D2 domain of slit (Structural insight into Slit-Robo signaling. Biochemical Society Transactions. 2008, 36: 251-256), therefore D2 domain is very important for the biology activity of Slit protein.

Chinese Patent CN201310150884.4 reports a fusion protein formed by D1-2 sequence of Slit2 protein prepared by using gene recombinant technology. The fusion protein helps LRR fold correctly and an active functional polypeptide form, which could be used for the research and application of Slit2 protein.

Protein drugs with a molecular weight less than 20 kD could be easily filtrated by glomerular in the metabolic process, leading to a short half-life in vivo. In order to achieve a therapeutic effect, a frequent or high dose administration is always required, which brings a great inconvenience to the patient. Human serum albumin (HSA) is a stable "inert" protein, and not easy to permeate through the glomerulus under normal physiological conditions with a half-life up to 14-21 days in serum, which can be used as a carrier binding with other factors in the blood including bioactive proteins, thereby maintaining or prolonging the bioactivity of other factors in vivo. It is an effective way to improve the half-life of small molecular peptides or protein drugs by the fusion of small molecular peptides or protein drugs with HSA. Compared with other methods, construction of a long-acting albumin fusion protein drug could avoid the complex chemical modification and processing, and thereby which could be easy to operate and have a better economic advantage.

In order to overcome the deficiencies in the prior art, the present invention provides a fusion protein for prophylaxis and/or treatment of sepsis and use thereof.

SUMMARY OF THE INVENTION

An object of the present invention is to provide a fusion protein for prophylaxis and/or treatment of sepsis, overcoming the deficiencies of biological drugs in the prior art with a larger molecular weight, a shorter half-life and a difficulty in drug development.

Another object of the present invention is to provide a drug for prophylaxis and/or treatment of sepsis which has a good therapeutic effect and could improve the survival rate of patients.

Therefore, the first aspect of the present invention provides a fusion protein formed by the fusion of a D2 domain of Slit2 protein and a HSA protein.

The said D2 domain of Slit2 protein in the invention, referred to as Slit2D2, comprises:
a) an amino acid sequence shown by SEQ ID NO: 1, or
b) an amino acid sequence with a same function obtained by substitution and/or deletion and/or addition of one or more amino acid residues of the aforesaid sequence a).

The said HSA in the invention comprises:
c) an amino acid sequence shown by SEQ ID NO: 2, or
d) an amino acid sequence with a same function obtained by substitution and/or deletion and/or addition of one or more amino acid residues of the aforesaid sequence c).

Preferably, in the fusion protein, there may be less than 10 amino acid residues changed for substitution and/or deletion and/or addition.

According to the invention, the connection of D2 domain of Slit2 protein with HSA protein is realized by a direct binding of C-terminal domain of former with the N-terminal domain of latter, or that of N-terminal domain of former with the C-terminal domain of latter, without any intermediate connecting peptide.

The said fusion protein in the invention contains an amino acid sequence shown by SEQ ID NO:3, or an amino acid sequence with a same function obtained by substitution and/or deletion and/or addition of one or more amino acid residues of the aforesaid sequence shown by SEQ ID NO:3.

The present invention also provides a gene encoding the said fusion protein Slit2D2-HSA comprising a nucleic acid sequence shown by SEQ ID NO:6, wherein the genes encoding D2 domain of Slit2 protein and HSA protein comprise a nucleic acid sequence shown by SEQ ID NO:4 SEQ ID NO:5, respectively.

Or, a DNA molecular obtained by hybridization with sequence shown by SEQ ID NO:6 under strict conditions which encodes a related protein with the ability for prophylaxis and/or treatment of sepsis; Or, a DNA molecular with at least not less than 90%, preferably not less than 95%, more preferably not less than 98% identify with sequence shown by SEQ ID NO:6 which encodes a related protein with the ability for prophylaxis and/or treatment of sepsis.

The present invention also provides a biological material related to Slit2D2-HSA fusion protein, including a recombinant vector, expression cassette, recombinant cell, recombinant bacteria and recombinant virus containing said gene encoding Slit2D2-HSA fusion protein. Preferably, the recombinant vector according to the present invention is a recombinant expression vector or a recombinant cloning vector.

Said fusion protein according to the present invention can be synthesized, or obtained by biological expression using synthetic coding gene.

The second aspect of the invention is to provide a method for preparation of the fusion protein comprising the following steps:
(1) constructing the recombinant vector;
(2) preparing and fermenting the transformant;
(3) isolating and purifying the fusion protein;
optionally, (4) identifying the fusion protein.

The aforesaid step (1) comprises the following specific steps:
obtaining the gene fragment of slit2D2 as a template by total gene synthesis, and then obtaining the gene sequence of slit2D2 with a length of 674 bp shown by SEQ ID NO: 4 by PCR amplification of primers T62F (with a sequence shown by SEQ ID NO: 7) and T62R (with a sequence shown by SEQ ID NO: 8);

obtaining the gene fragment of HSA as a template by total gene synthesis, and then obtaining the gene sequence of HSA with a length of 1783 bp shown by SEQ ID NO: 5 by PCR amplification of primers T60F3 (with a sequence shown by SEQ ID NO: 9) and T59R (with a sequence shown by SEQ ID NO: 10);

purifying and recovering the gene sequence of slit2D2 shown in SEQ ID NO: 4 and gene sequence of HSA shown by SEQ ID NO: 5 obtained by PCR amplification;

double-enzyme cleaving the plasmid vector containing CMV promoter by restriction endonuclease BssH II and EcoR I, and then conducting a seamless connection reaction of the gene of slit2D2 obtained after purification and recovery with the gene of HSA by using one step directed cloning kit;

transfecting the recombinant vector obtained after connection into the first host cell followed by transferring to a solid medium containing ampicillin (AMP) for breeding, screening the positive clones, confirming whether the construction of vector is successful by sequencing, and then preserving the strains.

The said vector plasmid is a pZD plasmid.

The first host cell includes but not limited to *E. coli* strain.

The aforesaid step (2) comprises the following specific steps:
extracting the recombinant plasmid from the first host cell;
culturing the second host cell, transfecting the recombinant vector extracted into the second host cell when the cell density reaches $2.5 \times 10^6$ cell/ml, determining the second host cell successfully transfected with the target gene as a transformant, and screening and fermenting the transformants, collecting the supernatant after 5 days.

The said recombinant vector is a plasmid pZD-Slit2D2-HSA.

The second host cell includes but not limited to EXPI293 cell.

The aforesaid step (3) comprises the following specific steps:
bringing the supernatant of culture medium collected in step (2), centrifuging at a high speed and then isolating and purifying the fusion protein Slit2D2-HSA.

The said purification refers to purification of protein by ion exchange chromatography.

The aforesaid step (4) comprises the following specific steps:
identifying the molecular weight, purity and bioactivity of the fusion protein.

The molecular weight of said fusion protein can be identified by general protein biochemical means including but not limited to SDS-PAGE, Western blotting and MS, etc.

The purity of said fusion protein is detected by SEC-HPLC.

The bioactivity of said fusion protein is assessed by measuring the affinity of fusion protein to the receptor Robo1.

The affinity of said fusion protein to the receptor Robo1 is measured by surface plasmon resonance (SPR) technique.

The third aspect of the present invention provides a pharmaceutical composition comprising said fusion protein Slit2D2-HSA formed by the fusion of D2 domain of Slit2 protein and HSA protein, and a pharmaceutically acceptable adjuvant.

The pharmaceutical compositions of the invention can be tablets (including sugar-coated tablets, film-coated tablets, sublingual tablets, orally disintegrating tablets, oral tablets, etc.), pills, powder, granules, capsules (including soft capsules, microcapsules), pastilles, syrups, liquids, emulsions, suspensions, controlled release formulations (e.g., instantaneous release formulations, sustained-release formulations, sustained-release microcapsules), aerosols, films (e.g., oral disintegrating films, oral mucosa adhesive films), injections (e.g., subcutaneous injections, intravenous injections, intramuscular injections, intraperitoneal injections), intravenous infusions, transdermal absorption formulations, ointments, lotions, adhesion agents, suppositories (e.g., rectal suppositories, vaginal suppositories), pillars, nasal preparations, lung preparations (inhalations), eye drops, etc., oral or parenteral formulations (e.g., intravenous, intramuscular, subcutaneous, organs, intranasal, intradermal, drip, brain, rectum and other forms of administration to the vicinity tumor and directly to the lesion place). Preferably, the said pharmaceutical composition is an injection.

The said pharmaceutically acceptable adjuvant in the present invention is preferably a pharmaceutically acceptable injectable adjuvant such as isotonic and sterile salt solution (sodium dihydrogen phosphate, disodium hydrogen phosphate, sodium chloride, potassium chloride, calcium chloride, magnesium chloride, etc., or mixtures of such salts), or injectable solutes formed by dried e.g., freeze-dried composition suitably dissolving in sterile water or saline.

The forth aspect of the present invention is to provide use of the fusion protein Slit2D2-HSA formed by fusion of D2 domain of Slit2 protein and HSA protein for prophylaxis and/or treatment of sepsis.

The fifth aspect of the present invention is to provide use of the fusion protein Slit2D2-HSA formed by fusion of D2 domain of Slit2 protein and HSA protein for the manufacture of a medicament for prophylaxis and/or treatment of sepsis. The said sepsis may be severe sepsis, septic shock.

In the present invention, the term "domain" refers to a region with a specific structure and independent function in a biological macromolecule, e.g., D2 domain of Slit2 protein refers to the second domain in four leucine-rich repeats in Slit2 protein.

In the present invention, the term "prophylaxis" or "treatment" includes the therapeutic or prophylactic treatment or measures with a purpose of preventing or slowing down the targeted pathological conditions or disorders. If a subject shows a reduction or disappearance of one or more signs and symptoms of a specific disease which can be observed and/or measured after being administered a therapeutic amount of the fusion protein according to the method of the present invention, the subject is successfully "prevented" or "treated".

The present invention makes the second leucine-rich repeat Slit2D2 in Slit 2 protein fused with HSA by gene engineering means to obtain a fusion protein Slit2D2-HSA with the pharmacological activities of Slit2 in inhibition of neutrophil migration and treatment of sepsis, an improved stability, prolonged half-life and improved therapeutic effect of sepsis; compared with protein of Slit2, the polypeptide of Slit2D2 has a smaller molecular weight which is much easier to be purified and separated in preparation and used in the development of drugs; the fusion protein Slit2D2-HSA according to the present invention has a higher therapeutic effect against sepsis, for CLP model in mice, the survival rate of animals in high dose group can reach 90%.

BRIEF DESCRIPTION OF THE DRAWINGS

FIG. 3 illustrates an experiment result of inhibition of neutrophil migration in vitro with fusion protein Slit2D2-HSA in rats;

DETAILED DESCRIPTION OF THE INVENTION

The following examples are provided to explain in greater detail the contents of the present invention. However, the content of the present invention is not limited to the following examples.

Example 1 Preparation of the Fusion Protein Slit2D2-HSA

The fusion expression vector of the second domain Slit2D2 (Hohenester2008) in Slit2 and HSA was analyzed, designed and constructed based on the known sequence of Slit2 [GenBank: EAW92793.1].

The gene fragment of slit2D2, as a template, was obtained by total gene synthesis, and then the gene sequence of slit2D2 with a length of 674 bp shown by SEQ ID NO: 4 was obtained by PCR amplification of primers T62F (with a sequence shown by SEQ ID NO: 7) and T62R (with a sequence shown by SEQ ID NO: 8).

The gene fragment of HSA, as a template, was obtained by total gene synthesis, and then the gene sequence of HSA with a length of 1783 bp shown by SEQ ID NO: 5 was obtained by PCR amplification of primers T60F3 (with a sequence shown by SEQ ID NO: 9) and T59R (with a sequence shown by SEQ ID NO: 10).

The gene sequence of slit2D2 shown in SEQ ID NO: 4 and gene sequence of HSA shown by SEQ ID NO: 5 obtained by PCR amplification were purified and recovered.

The plasmid vector containing CMV promoter was double-enzyme digested by restriction endonuclease BssH II and EcoR I, and then a seamless connection reaction of the gene of slit2D2 obtained after purification and recovery with the gene of HSA was conducted by using one step directed cloning kit. The recombinant vector was transfected into *E. coli* Top10 followed by being transferred to a solid medium containing ampicillin (AMP) for breeding, the positive clones were screened, whether the construction of vector is successful was confirmed by sequencing, and then the strains were preserved.

The recombinant plasmid in *E. coli* TOP10 was extracted by using endo-free plasmid extraction kit, and was then transfected into EXPI293 cells when the cell density of EXPI293 cells reached $2.5 \times 10^6$ cell/ml. The supernatant of culture medium was collected and centrifuged at a high speed after being cultured for 5 days. The fusion protein Slit2D2-HSA was purified by a HiTrap Q HP anion column, and the molecular weight and purity of Slit2D2-HSA were detected by SDS-PAGE and SEC-HPLC, respectively.

Figure 1:
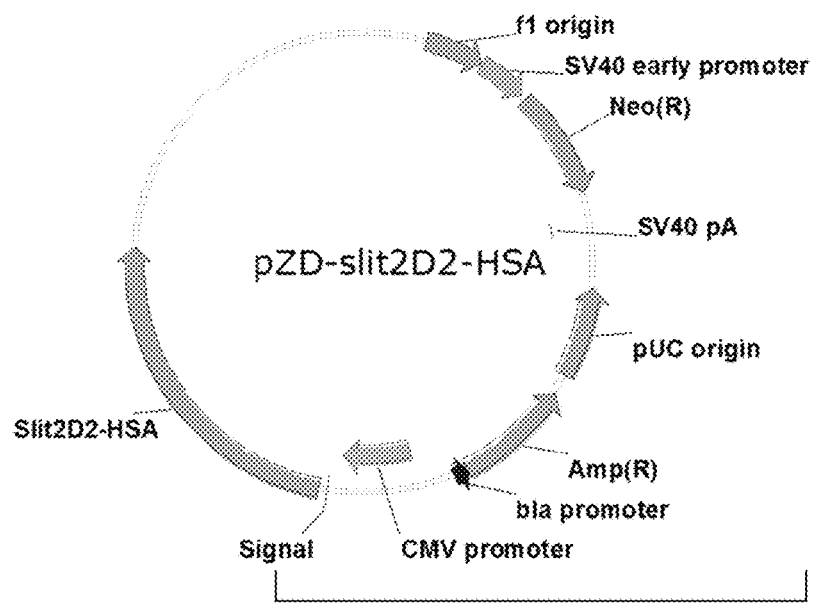
FIG. 1 illustrates a map of recombinant plasmid pZD-Slit2D2-HSA containing the fusion protein Slit2D2-HSA.
Figure 2:
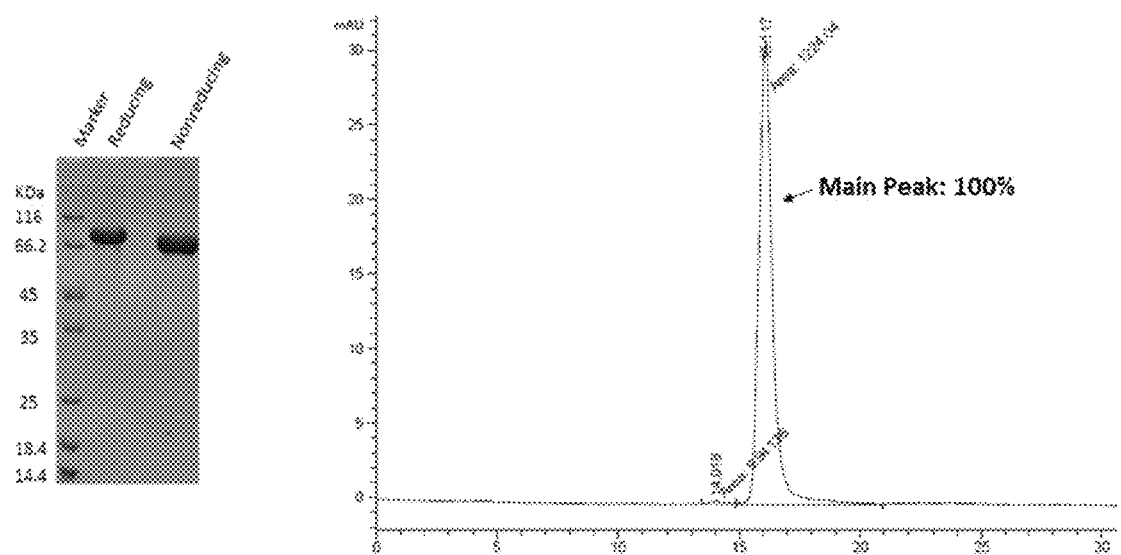
FIG. 2 illustrates a graph of identification results of expression of the fusion protein Slit2D2-HSA; wherein the left graph is a 12% SDS-PAGE electrophoretogram of the fusion protein Slit2D2-HSA; the right graph is a SEC-HPLC spectra of the fusion protein Slit2D2-HSA using G3000swxl gel column with a flow rate of 0.5 ml/min, a period of 40 min and a detector of UV280.

Wherein, the result of SDS-PAGE and the SEC-HPLC spectra are shown in FIG. 2. It is proved by FIG. 2 that a recombinant expression vector containing fusion protein Slit2D2-HSA was constructed successfully and the expression and purification of the fusion protein Slit2D2-HSA in the host cell was achieved.

Example 2 Affinity of Fusion Protein Slit2D2-HSA to Target Protein Robo1 Determined by SPR The affinity constant between the prepared protein and Robo1 was determined by SPR (Surface Plasmon resonance BIAcore200). The Robo1 (ORIGEN Company, number: TP327713) was bound on CM5 chip and used to analysis the interaction between fusion protein Slit2D2-HSA and receptor Robo1. Kinetic measurements were carried out according to the method referred by Canziani et al. (2004, Anal. Biochem. 325:301-307), simultaneously, the same method was applied to measure the affinity between Slit2N protein (Slit2N is a protein at N-terminal of slit2 with a molecular weight of about 120 KDa) and Robo1.

TABLE 1

Result of affinity of fusion protein Slit2D2-HSA to receptor Robo1 measured by SPR

| No. | Protein | Ka (1/Ms) | KD (M) | Kd (nM) |
|---|---|---|---|---|
| 1 | Slit2N | $7.436 \times 10^5$ | $3.394 \times 10^{-3}$ | 4.5 |
| 2 | Slit2D2-HSA | $1.771 \times 10^5$ | $5.099 \times 10^{-4}$ | 2.8 |

The experiment results showed that the constructed fusion protein Slit2D2-HSA had a good affinity to Robo1, which was similar to the property of Slit2N.

Example 3 Experiment of Inhibition of Neutrophil Migration In Vitro with Fusion Protein Slit2D2-HSA in Rats Extraction of Rat Neutrophils 16 ml of fresh anticoagulation was taken from rat and then mixed with 16 ml of tissue dilution. Every 2 ml of the mixture obtained was added into 10 ml EP tube containing 2 ml of liquid A of neutrophils extraction kit, followed by being centrifuged at 500 g for 25 min for stratify. Then cells in the first and second layer were discarded, meanwhile cells in the third and forth layer were collected and placed into a test tube containing 10 ml of cell washing liquid, followed by being centrifuged at 500 g for 30 min to remove the supernatant. Then 3-5 times the cell volume of red blood cell lysate was added into the precipitation and the mixture was mixed, and cell lysis was performed for 1-2 min. The mixture obtained was centrifuged at 500 g for 5 min and then the supernatant was discarded. The cell lysis was repeated once. Washing was performed 1-2 times as follows: proper amount of PBS solution was added to make the precipitate resuspended and then the mixture obtained was centrifuged at 500 g for 3 min to remove the supernatant. The precipitate was resuspended by 1640 complete medium and transferred to a 6 cm plate, rat neutrophils were extracted successfully and incubated in an incubator.

The neutrophils were resuspended after centrifugation, and then $1 \times 10^6$ cells were added into the upper transwell chamber followed by adding 100 μl of BSA (10 mg/ml) without serum and corresponding drugs as shown in FIG. 3, while 600 μl medium containing serum and 10 mg/ml of BSA was added into the sublayer, except the PBS group, other groups were added by fMLP with a final concentration of 100 μM. 3 hours later, the chamber was taken out and cells in the lower culture medium were centrifuged, collected and concentrated 6 times by being suspended in 100 μl of PBS, and then added into a blood cell counting chamber for counting, the total number of cells in four large squares, upper left square, upper right square, lower left square and lower right square, were statistic calculated.

Experimental results showed that, as shown in FIG. 3, the fusion protein Slit2D2-HSA could significantly inhibit rat neutrophil migration (P<0.01) in vitro, and had a better activity of inhibiting neutrophil migration.

Example 4 Experiment of Inhibition of LPS-Induced Neutrophil Migration with Fusion Protein Slit2D2-HSA in Rats with Acute Lung Injury Acute lung injury (ALI) is an uncontrolled systemic inflammatory response caused by varieties of direct or indirect injury factors, accompanied by damage of alveolar epithelial cells and capillary endothelial cells. The pathogenesis of ALI is not clear, and currently, there is a lack of effective treatment means for ALI. In the present invention, ALI is induced by intratracheal lipopolysaccharide (LPS) infusion in rats which is a commonly used animal model. Animals were injected compounds via tail vein and 4 hours later, the fluid of lung lavage and bronchioalveolar lavage were collected and used for measurement by COMP-U-DIFF, and the measurement results represented the efficacy of testing compounds in prevention of LPS-induced ALI. The experiment design of animal grouping is shown in Table 2.

Figure 4:
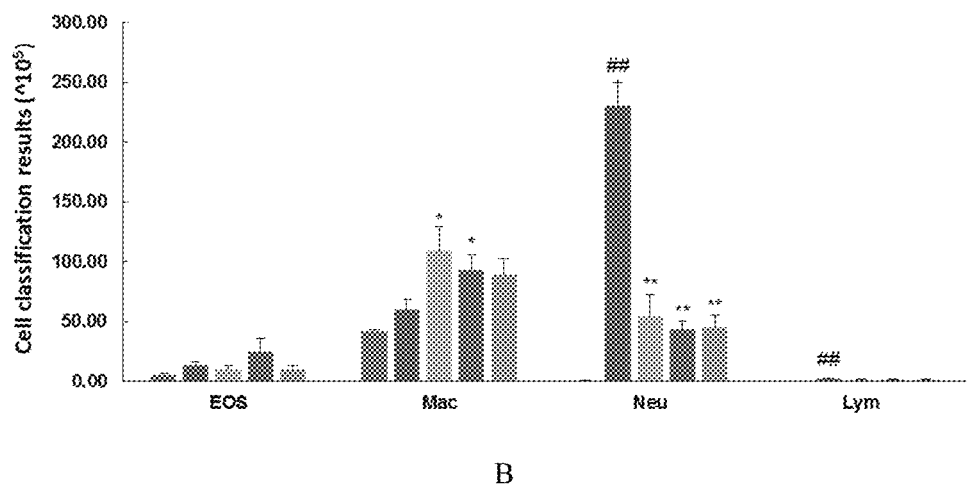
FIG. 4 illustrates an experiment result of inhibition of LPS-induced cell migration with fusion protein Slit2D2-HSA in rats with acute lung injury; wherein the figure A illustrates a result of total cell number; the figure B illustrates a result of the numbers of eosinophils (EOS), macrophages (Mac), neutrophils (Neu) and lymphocytes (Lym), in figure B, the results of each group are normal control group, solvent group, dexamethasone group, fusion protein Slit2D2-HSA 1 mg/kg, fusion protein Slit2D2-HSA 5 mg/kg, from left to right, respectively.
Figure 5:
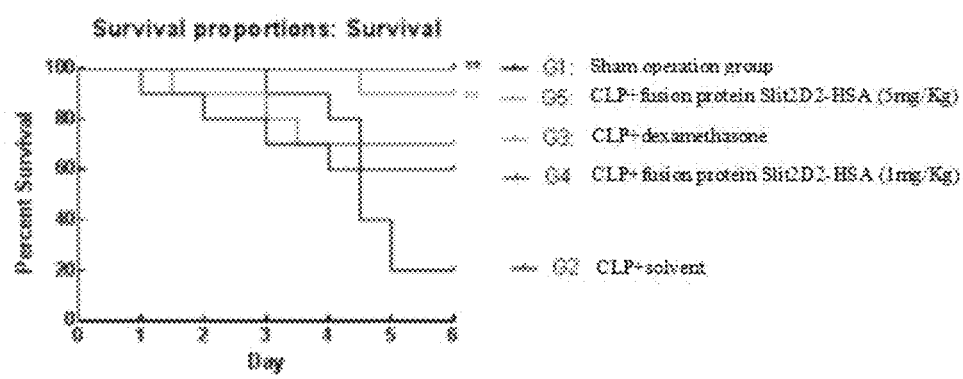
FIG. 5 illustrates an efficacy test result of CLP sepsis model of fusion protein Slit2D2-HSA, and ** indicates a p-value less than 0.01 compared with G2 group: CLP+ solvent (wilcoxon test)

In addition to the first group, other groups of animals were treated with lipopolysaccharide lung perfusion. Concretely, using a micro-cannula sprayer, 100 μl of LPS solution (1 mg/ml) was imported into the tracheal cannula of rats which were anesthetized with 3-5% isoflurane in advance, and 4 hours later the animals were sacrificed using chloral hydrate (750 mg/kg). Lung lavage were carried out three times in situ using 4 ml of PBS+1% albumin. After lavage, bronchioalveolar lavage fluid (BALF) was stored in ice and then the amount of eosinophils (EOS), macrophages (Mac), neutrophils (Neu), lymphocytes (Lym) and total cells were counted. The results of total cell number of 5 groups are illustrated in FIG. 4 and the number of EOS, Mac, Neu and Lym are shown in FIG. 5.

In this study, the total cell number of the second group, as LPS model group, had an increase, while the number of neutrophils and the total cells decreased significantly with dexamethasone at a dosage of 10 mg/kg as a positive control. Compared with the model group, fusion protein Slit2D2-HSA at a dosage of 1 mg/kg and 5 mg/kg could significantly inhibit the increase of cell number and control the number of neutrophils.

TABLE 2

Experiment of inhibition of neutrophil migration with fusion protein Slit2D2-HSA

| Group | Test agent | Number of rats | Administration route | Concentrate mg/mL | Dosage mL/kg | Dosage mg/kg | Dosage regimen |
|---|---|---|---|---|---|---|---|
| 1 | Normal control group | 3 | N/A | 0 | 0 | 0 | N/A |
| 2 | solvent | 6 | intravenous drip | TBD | 10 | TBD | TBD |
| 3 | dexamethasone | 6 | oral | 1 | 10 | 10 | 3 hours before LPS infusion, oral |
| 4 | fusion protein Slit2D2-HSA | 6 | intravenous drip | 0.5 | 2 | 1 | 3 hours before LPS infusion, intravenous drip |
| 5 | fusion protein Slit2D2-HSA | 6 | intravenous drip | 2.5 | 2 | 5 | 3 hours before LPS infusion, intravenous drip |

Example 5 Detection of Therapeutic Effect on CLP Sepsis Model

The cecalligation-peferation (CLP) test of rodent was widely adopted to build an experimental sepsis model. This experiment evaluated the efficacy of testing drugs on CLP sepsis induced in C57BL/6 mice.

The CLP surgery was conducted on six to eight-week-old male C57BL/6SDF mice weighed 18-22 g as experiment animals. Mice were anesthetized by intraperitoneal injection of ketamine (50 mg/kg body weight), and an incision with a length of 1 cm was made in the ventral midline of the mice, mesenteric and cecum were dissociated, and the end of cecum was ligated with a 4-silk suture at 1.2 cm from the tip of cecum. Subsequently, the end of the cecum was pierced for two times with a sterile 21-needle, and a little excreta was squeezed into the abdominal cavity, and then intestinal segment was returned and the peritoneal and skin were stitched in turn. Animal grouping and drug administration are described as the following table 3, and the death status of each group were observed and recorded.

The experimental results are shown in FIG. 5, and FIG. 5 shows that the survive rate of CLP model was significantly increased by tail intravenous administration of fusion protein Slit2D2-HSA. The survive rate of CLP model animal reached 90% at a dosage of 5 mg/kg, while the control group only reached 20%, which indicated that the fusion protein Slit2D2-HSA had a good therapeutic effect on the sepsis and could be an effective drug for prophylaxis and treatment of sepsis.

Example 6 Safety Evaluation of the Fusion Protein Slit2D2-HSA

In order to evaluate the safety of the fusion protein Slit2D2-HSA in animals sufficiently, mice were administered continuous, and the changes of body weight and the survival status of the mice were observed to evaluate the effect of drugs on mice.

TABLE 3

Detection experiment of therapeutic effect of Slit2D2-HSA on CLP sepsis model

| Group | Testing agent | Number of rats | Administration route | Concentration mg/mL | Dosage mL/kg | Dosage mg/kg | Dosage regimen |
|---|---|---|---|---|---|---|---|
| 1 | sham operating group | 10 | N/A | 1 | 10 | 0 | N/A |
| 2 | CLP + solvent | 10 | intraperitoneal injection | 1 | 10 | 0 | 0-6 day, Once a day an hour before CLP |
| 3 | CLP + dexamethasone | 10 | oral | 1 | 10 | 10 | surgeon and postoperative 18 hours each time |
| 4 | CLP + Slit2D2-HSA | 10 | intraperitoneal injection | 0.1 | 10 | 1 | 0-6 days, once a day |
| 5 | CLP + Slit2D2-HSA | 10 | intraperitoneal injection | 0.5 | 10 | 5 | 0-6 days, once a day |

TABLE 4

Safety evaluation experiment of the fusion protein Slit2D2-HSA

| Group | Treatment | Dose | Dosage regimen | Administration route | Number of mice |
|---|---|---|---|---|---|
| 1 | solvent(PBS) | 0 | daily/30 days | intraperitoneal injection | 10 |
| 2 | Slit2D2-HSA | 10 mg/kg | daily/30 days | intraperitoneal injection | 10 |
| 3 | Slit2D2-HSA | 5 mg/kg | daily/30 days | intraperitoneal injection | 10 |
| 4 | Slit2D2-HSA | 1 mg/kg | daily/30 days | intraperitoneal injection | 10 |

Figure 6:
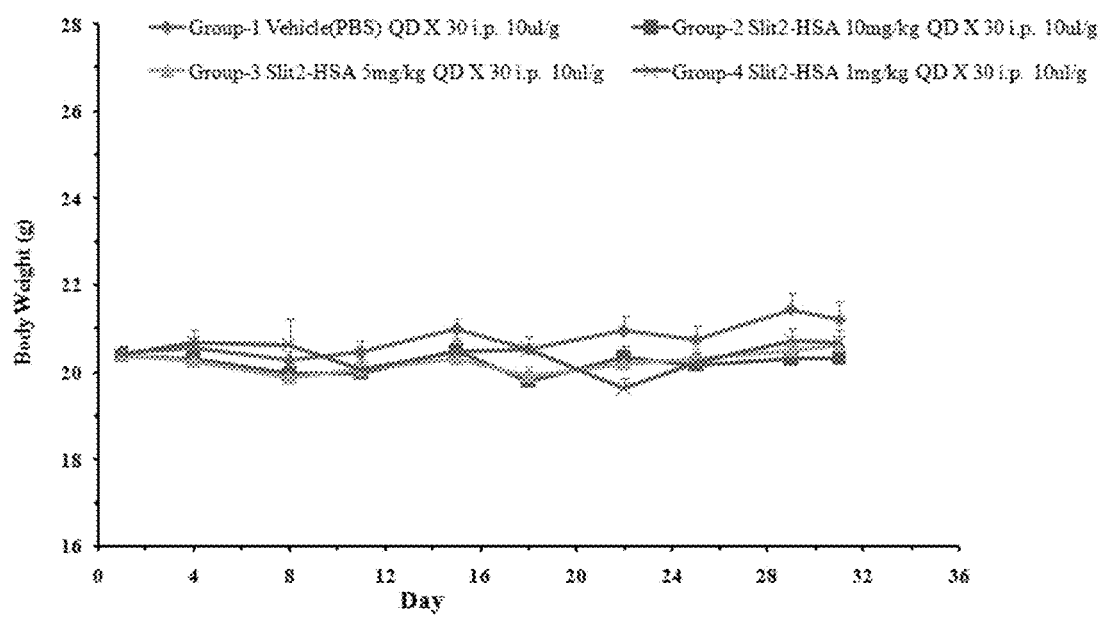
FIG. 6 illustrates a safety evaluation result of the fusion protein Slit2D2-HSA.

The results of body weight changes over time of four group mice are shown in FIG. 6. The figure shows that there was no significant change in body weight in the three dose groups and animals were in good condition after 30 days of intravenous administration of tail vein in mice, which indicated a good drug safety of fusion protein Slit2D2-HSA.

The invention claimed is:

1. A fusion protein Slit2D2-HSA formed by the fusion of a D2 domain of Slit2 protein and a HSA protein;
   wherein said D2 domain of Slit2 comprises:
   a) an amino acid sequence shown by SEQ ID NO: 1, or
   b) an amino acid sequence with a same function obtained by substitution and/or deletion and/or addition of one or more amino acid residues of the aforesaid sequence a);
   said HSA comprises:
   c) an amino acid sequence shown by SEQ ID NO: 2, or
   d) an amino acid sequence with a same function obtained by substitution and/or deletion and/or addition of one or more amino acid residues of the aforesaid sequence c);
   wherein the C-terminal domain of said D2 domain of Slit2 is directly linked to the N-terminal domain of said HSA protein, or the N-terminal domain of said D2 domain of Slit2 is directly linked to the C-terminal domain of said HSA protein; and wherein up to 10 amino acid residues are changed for substitution and/or deletion and/or addition.

2. The fusion protein Slit2D2-HSA of claim 1, wherein the fusion protein contains an amino acid sequence shown by SEQ ID NO: 3, or, an amino sequence with a same function obtained by substitution and/or deletion and/or addition of one or more amino acid residues of the aforesaid sequence shown by SEQ ID NO: 3.

3. A method of prophylaxis and/or treatment of sepsis comprising the steps of:
   preparing a pharmaceutically acceptable composition or a pharmaceutically acceptable adjuvant comprising the fusion protein Slit2D2-HSA formed by fusion of the D2 domain of Slit2 protein and HSA protein as in claim 1, and administering the composition or adjuvant to a subject for the prophylaxis or treatment thereof.

4. The method of claim 3, wherein the sepsis is severe sepsis; or septic shock.

* * * * *

SEQUENCE LISTING

```
<160> NUMBER OF SEQ ID NOS: 10

<210> SEQ ID NO 1
<211> LENGTH: 209
<212> TYPE: PRT
<213> ORGANISM: Artificial Sequence
<220> FEATURE:
<223> OTHER INFORMATION: D2 domain of Slit2 protein

<400> SEQUENCE: 1

Leu His Cys Pro Ala Ala Cys Thr Cys Ser Asn Asn Ile Val Asp Cys
1               5                   10                  15

Arg Gly Lys Gly Leu Thr Glu Ile Pro Thr Asn Leu Pro Glu Thr Ile
            20                  25                  30

Thr Glu Ile Arg Leu Glu Gln Asn Thr Ile Lys Val Ile Pro Pro Gly
        35                  40                  45

Ala Phe Ser Pro Tyr Lys Lys Leu Arg Arg Ile Asp Leu Ser Asn Asn
    50                  55                  60

Gln Ile Ser Glu Leu Ala Pro Asp Ala Phe Gln Gly Leu Arg Ser Leu
65                  70                  75                  80

Asn Ser Leu Val Leu Tyr Gly Asn Lys Ile Thr Glu Leu Pro Lys Ser
                85                  90                  95

Leu Phe Glu Gly Leu Phe Ser Leu Gln Leu Leu Leu Asn Ala Asn
                100                 105                 110

Lys Ile Asn Cys Leu Arg Val Asp Ala Phe Gln Asp Leu His Asn Leu
            115                 120                 125

Asn Leu Leu Ser Leu Tyr Asp Asn Lys Leu Gln Thr Ile Ala Lys Gly
        130                 135                 140

Thr Phe Ser Pro Leu Arg Ala Ile Gln Thr Met His Leu Ala Gln Asn
145                 150                 155                 160

Pro Phe Ile Cys Asp Cys His Leu Lys Trp Leu Ala Asp Tyr Leu His
                165                 170                 175

Thr Asn Pro Ile Glu Thr Ser Gly Ala Arg Cys Thr Ser Pro Arg Arg
                180                 185                 190

Leu Ala Asn Lys Arg Ile Gly Gln Ile Lys Ser Lys Lys Phe Arg Cys
            195                 200                 205

Ser

<210> SEQ ID NO 2
<211> LENGTH: 585
<212> TYPE: PRT
<213> ORGANISM: Artificial Sequence
<220> FEATURE:
<223> OTHER INFORMATION: Human serum albumin protein
```

<400> SEQUENCE: 2

```
Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
                20                  25                  30

Gln Cys Pro Phe Glu Asp His Val Lys Leu Val Asn Glu Val Thr Glu
            35                  40                  45

Phe Ala Lys Thr Cys Val Ala Asp Glu Ser Ala Glu Asn Cys Asp Lys
        50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
```

```
                    405                 410                 415
Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
            435                 440                 445

Ala Glu Asp Tyr Leu Ser Val Val Leu Asn Gln Leu Cys Val Leu His
            450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
            515                 520                 525

Leu Val Glu Leu Val Lys His Lys Pro Lys Ala Thr Lys Glu Gln Leu
            530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu
            580                 585

<210> SEQ ID NO 3
<211> LENGTH: 794
<212> TYPE: PRT
<213> ORGANISM: Artificial Sequence
<220> FEATURE:
<223> OTHER INFORMATION: Fusion protein Slit2D2-HSA

<400> SEQUENCE: 3

Leu His Cys Pro Ala Ala Cys Thr Cys Ser Asn Asn Ile Val Asp Cys
1               5                   10                  15

Arg Gly Lys Gly Leu Thr Glu Ile Pro Thr Asn Leu Pro Glu Thr Ile
            20                  25                  30

Thr Glu Ile Arg Leu Glu Gln Asn Thr Ile Lys Val Ile Pro Pro Gly
        35                  40                  45

Ala Phe Ser Pro Tyr Lys Lys Leu Arg Arg Ile Asp Leu Ser Asn Asn
    50                  55                  60

Gln Ile Ser Glu Leu Ala Pro Asp Ala Phe Gln Gly Leu Arg Ser Leu
65                  70                  75                  80

Asn Ser Leu Val Leu Tyr Gly Asn Lys Ile Thr Glu Leu Pro Lys Ser
                85                  90                  95

Leu Phe Glu Gly Leu Phe Ser Leu Gln Leu Leu Leu Leu Asn Ala Asn
            100                 105                 110

Lys Ile Asn Cys Leu Arg Val Asp Ala Phe Gln Asp Leu His Asn Leu
        115                 120                 125

Asn Leu Leu Ser Leu Tyr Asp Asn Lys Leu Gln Thr Ile Ala Lys Gly
    130                 135                 140

Thr Phe Ser Pro Leu Arg Ala Ile Gln Thr Met His Leu Ala Gln Asn
145                 150                 155                 160

Pro Phe Ile Cys Asp Cys His Leu Lys Trp Leu Ala Asp Tyr Leu His
                165                 170                 175

Thr Asn Pro Ile Glu Thr Ser Gly Ala Arg Cys Thr Ser Pro Arg Arg
```

```
            180                 185                 190
Leu Ala Asn Lys Arg Ile Gly Gln Ile Lys Ser Lys Lys Phe Arg Cys
            195                 200                 205

Ser Asp Ala His Lys Ser Glu Val Ala His Arg Phe Lys Asp Leu Gly
            210                 215                 220

Glu Glu Asn Phe Lys Ala Leu Val Leu Ile Ala Phe Ala Gln Tyr Leu
225                 230                 235                 240

Gln Gln Cys Pro Phe Glu Asp His Val Lys Leu Val Asn Glu Val Thr
                245                 250                 255

Glu Phe Ala Lys Thr Cys Val Ala Asp Glu Ser Ala Glu Asn Cys Asp
            260                 265                 270

Lys Ser Leu His Thr Leu Phe Gly Asp Lys Leu Cys Thr Val Ala Thr
            275                 280                 285

Leu Arg Glu Thr Tyr Gly Glu Met Ala Asp Cys Cys Ala Lys Gln Glu
            290                 295                 300

Pro Glu Arg Asn Glu Cys Phe Leu Gln His Lys Asp Asp Asn Pro Asn
305                 310                 315                 320

Leu Pro Arg Leu Val Arg Pro Glu Val Asp Val Met Cys Thr Ala Phe
                325                 330                 335

His Asp Asn Glu Glu Thr Phe Leu Lys Lys Tyr Leu Tyr Glu Ile Ala
            340                 345                 350

Arg Arg His Pro Tyr Phe Tyr Ala Pro Glu Leu Leu Phe Phe Ala Lys
            355                 360                 365

Arg Tyr Lys Ala Ala Phe Thr Glu Cys Cys Gln Ala Ala Asp Lys Ala
            370                 375                 380

Ala Cys Leu Leu Pro Lys Leu Asp Glu Leu Arg Asp Glu Gly Lys Ala
385                 390                 395                 400

Ser Ser Ala Lys Gln Arg Leu Lys Cys Ala Ser Leu Gln Lys Phe Gly
                405                 410                 415

Glu Arg Ala Phe Lys Ala Trp Ala Val Ala Arg Leu Ser Gln Arg Phe
            420                 425                 430

Pro Lys Ala Glu Phe Ala Glu Val Ser Lys Leu Val Thr Asp Leu Thr
            435                 440                 445

Lys Val His Thr Glu Cys Cys His Gly Asp Leu Leu Glu Cys Ala Asp
            450                 455                 460

Asp Arg Ala Asp Leu Ala Lys Tyr Ile Cys Glu Asn Gln Asp Ser Ile
465                 470                 475                 480

Ser Ser Lys Leu Lys Glu Cys Cys Glu Lys Pro Leu Leu Glu Lys Ser
                485                 490                 495

His Cys Ile Ala Glu Val Glu Asn Asp Glu Met Pro Ala Asp Leu Pro
            500                 505                 510

Ser Leu Ala Ala Asp Phe Val Glu Ser Lys Asp Val Cys Lys Asn Tyr
            515                 520                 525

Ala Glu Ala Lys Asp Val Phe Leu Gly Met Phe Leu Tyr Glu Tyr Ala
            530                 535                 540

Arg Arg His Pro Asp Tyr Ser Val Val Leu Leu Leu Arg Leu Ala Lys
545                 550                 555                 560

Thr Tyr Glu Thr Thr Leu Glu Lys Cys Cys Ala Ala Ala Asp Pro His
                565                 570                 575

Glu Cys Tyr Ala Lys Val Phe Asp Glu Phe Lys Pro Leu Val Glu Glu
            580                 585                 590

Pro Gln Asn Leu Ile Lys Gln Asn Cys Glu Leu Phe Glu Gln Leu Gly
            595                 600                 605
```

```
Glu Tyr Lys Phe Gln Asn Ala Leu Leu Val Arg Tyr Thr Lys Lys Val
    610                 615                 620
Pro Gln Val Ser Thr Pro Thr Leu Val Glu Val Ser Arg Asn Leu Gly
625                 630                 635                 640
Lys Val Gly Ser Lys Cys Cys Lys His Pro Glu Ala Lys Arg Met Pro
                645                 650                 655
Cys Ala Glu Asp Tyr Leu Ser Val Val Leu Asn Gln Leu Cys Val Leu
                660                 665                 670
His Glu Lys Thr Pro Val Ser Asp Arg Val Thr Lys Cys Cys Thr Glu
            675                 680                 685
Ser Leu Val Asn Arg Arg Pro Cys Phe Ser Ala Leu Glu Val Asp Glu
        690                 695                 700
Thr Tyr Val Pro Lys Glu Phe Asn Ala Glu Thr Phe Thr Phe His Ala
705                 710                 715                 720
Asp Ile Cys Thr Leu Ser Glu Lys Glu Arg Gln Ile Lys Lys Gln Thr
                725                 730                 735
Ala Leu Val Glu Leu Val Lys His Lys Pro Lys Ala Thr Lys Glu Gln
                740                 745                 750
Leu Lys Ala Val Met Asp Asp Phe Ala Ala Phe Val Glu Lys Cys Cys
            755                 760                 765
Lys Ala Asp Asp Lys Glu Thr Cys Phe Ala Glu Glu Gly Lys Lys Leu
        770                 775                 780
Val Ala Ala Ser Gln Ala Ala Leu Gly Leu
785                 790
```

```
<210> SEQ ID NO 4
<211> LENGTH: 627
<212> TYPE: DNA
<213> ORGANISM: Artificial Sequence
<220> FEATURE:
<223> OTHER INFORMATION: Nucleic acid encoding the D2 domain of Slit2
      protein

<400> SEQUENCE: 4
ttgcactgcc ctgccgcctg tacctgtagc aacaatatcg tagactgtcg tgggaaaggt      60
ctcactgaga tccccacaaa tcttccagag accatcacag aaatacgttt ggaacagaac     120
acaatcaaag tcatccctcc tggagctttc tcaccatata aaaagcttag acgaattgac     180
ctgagcaata atcagatctc tgaacttgca ccagatgctt tccaaggact acgctctctg     240
aattcacttg tcctctatgg aaataaaatc acagaactcc ccaaaagttt atttgaagga     300
ctgttttcct tacagctcct attattgaat gccaacaaga taaactgcct tcgggtagat     360
gcttttcagg atctccacaa cttgaacctt ctctccctat atgacaacaa gcttcagacc     420
atcgccaagg ggacctttc acctcttcgg gccattcaaa ctatgcattt ggcccagaac     480
cccttatttt gtgactgcca tctcaagtgg ctagcggatt atctccatac caacccgatt     540
gagaccagtg gtgcccgttg caccagcccc cgccgcctgg caaacaaaag aattggacag     600
atcaaaagca agaaattccg ttgttca                                          627
```

```
<210> SEQ ID NO 5
<211> LENGTH: 1758
<212> TYPE: DNA
<213> ORGANISM: Artificial Sequence
<220> FEATURE:
<223> OTHER INFORMATION: Nucleic acid encoding the human serum albumin
      protein
```

<400> SEQUENCE: 5

```
gatgcacaca agagtgaggt tgctcatcgg tttaaagatt tgggagaaga aaatttcaaa        60
gccttggtgt tgattgcctt tgctcagtat cttcagcagt gtccatttga agatcatgta       120
aaattagtga atgaagtaac tgaatttgca aaaacatgtg ttgctgatga gtcagctgaa       180
aattgtgaca atcacttca tacccttttt ggagacaaat tatgcacagt tgcaactctt        240
cgtgaaacct atggtgaaat ggctgactgc tgtgcaaaac aagaacctga gagaaatgaa       300
tgcttcttgc aacacaaaga tgacaaccca aacctccccc gattggtgag accagaggtt       360
gatgtgatgt gcactgcttt tcatgacaat aagagacat ttttgaaaaa atacttatat        420
gaaattgcca aagacatcc ttactttat gccccggaac tccttttctt tgctaaaagg         480
tataaagctg cttttacaga atgttgccaa gctgctgata agctgcctg cctgttgcca        540
aagctcgatg aacttcggga tgaagggaag gcttcgtctg ccaaacagag actcaagtgt       600
gccagtctcc aaaaatttgg agaaagagct ttcaaagcat gggcagtagc tcgcctgagc       660
cagagatttc ccaaagctga gtttgcagaa gtttccaagt tagtgacaga tcttaccaaa       720
gtccacacgg aatgctgcca tggagatctg cttgaatgtg ctgatgacag ggcggacctt       780
gccaagtata tctgtgaaaa tcaagattcg atctccagta aactgaagga atgctgtgaa       840
aaacctctgt tggaaaaatc ccactgcatt gccgaagtgg aaaatgatga gatgcctgct       900
gacttgcctt cattagctgc tgattttgtt gaaagtaagg atgtttgcaa aaactatgct       960
gaggcaaagg atgtcttcct gggcatgttt ttgtatgaat atgcaagaag gcatcctgat      1020
tactctgtcg tgctgctgct gagacttgcc aagacatatg aaaccactct agagaagtgc      1080
tgtgccgctg cagatcctca tgaatgctat gccaaagtgt tcgatgaatt taaacctctt      1140
gtggaagagc tcagaatttt aatcaaacaa aattgtgagc tttttgagca gcttggagag      1200
tacaaattcc agaatgcgct attagttcgt tacaccaaga agtaccccca agtgtcaact      1260
ccaactcttg tagaggtctc aagaaaccta ggaaaagtgg gcagcaaatg ttgtaaacat      1320
cctgaagcaa aaagaatgcc ctgtgcagaa gactatctat ccgtggtcct gaaccagtta      1380
tgtgtgttgc atgagaaaac gccagtaagt gacagagtca ccaaatgctg cacagaatcc      1440
ttggtgaaca ggcgaccatg cttttcagct ctggaagtcg atgaaacata cgttcccaaa      1500
gagtttaatg ctgaaacatt caccttccat gcagatatat gcacactttc tgagaaggag      1560
agacaaatca gaaacaaac tgcacttgtt gagctcgtga acacaagcc caaggcaaca       1620
aaagagcaac tgaaagctgt tatggatgat ttcgcagctt ttgtagagaa gtgctgcaag      1680
gctgacgata aggagacctg cttttgccgag gagggtaaaa aacttgttgc tgcaagtcaa      1740
gctgccttag gcttataa                                                    1758
```

<210> SEQ ID NO 6
<211> LENGTH: 2385
<212> TYPE: DNA
<213> ORGANISM: Artificial Sequence
<220> FEATURE:
<223> OTHER INFORMATION: Nucleic acid encoding the fusion protein Slit2D2-HSA

<400> SEQUENCE: 6

```
ttgcactgcc ctgccgcctg tacctgtagc aacaatatcg tagactgtcg tgggaaaggt        60
ctcactgaga tccccacaaa tcttccagag accatcacag aaatacgttt ggaacagaac       120
acaatcaaag tcatccctcc tggagctttc tcaccatata aaaagcttag acgaattgac       180
```

```
ctgagcaata atcagatctc tgaacttgca ccagatgctt tccaaggact acgctctctg    240
aattcacttg tcctctatgg aaataaaatc acagaactcc ccaaaagttt atttgaagga    300
ctgttttcct tacagctcct attattgaat gccaacaaga taaactgcct tcgggtagat    360
gcttttcagg atctccacaa cttgaacctt ctctccctat atgacaacaa gcttcagacc    420
atcgccaagg ggacctttc acctcttcgg gccattcaaa ctatgcattt ggcccagaac     480 cccttatt gtgactgcca tctcaagtgg ctagcggatt atctccatac caacccgatt     540
gagaccagtg gtgcccgttg caccagcccc cgccgcctgg caaacaaaag aattggacag    600
atcaaaagca agaaattccg ttgttcagat gcacacaaga gtgaggttgc tcatcggttt    660
aaagatttgg gagaagaaaa tttcaaagcc ttggtgttga ttgcctttgc tcagtatctt    720
cagcagtgtc catttgaaga tcatgtaaaa ttagtgaatg aagtaactga atttgcaaaa    780
acatgtgttg ctgatgagtc agctgaaaat tgtgacaaat cacttcatac ccttttgga    840 gacaaattat gcacagttgc aactcttcgt gaaacctatg gtgaaatggc tgactgctgt    900
gcaaaacaag aacctgagag aaatgaatgc ttcttgcaac acaaagatga cacccaaac    960 ctcccccgat tggtgagacc agaggttgat gtgatgtgca ctgcttttca tgacaatgaa   1020
gagacatttt tgaaaaaata cttatatgaa attgccagaa gacatcctta cttttatgcc    1080
ccggaactcc ttttctttgc taaaaggtat aaagctgctt ttacagaatg ttgccaagct    1140
gctgataaag ctgcctgcct gttgccaaag ctcgatgaac ttcggatgga agggaaggct    1200
tcgtctgcca aacagagact caagtgtgcc agtctccaaa aatttggaga aagagctttc    1260
aaagcatggg cagtagctcg cctgagccag agatttccca agctgagtt tgcagaagtt    1320 tccaagttag tgacagatct taccaaagtc cacacggaat gctgccatgg agatctgctt    1380
gaatgtgctg atgacagggc ggaccttgcc aagtatatct gtgaaaatca agattcgatc    1440
tccagtaaac tgaaggaatg ctgtgaaaaa cctctgttgg aaaaatccca ctgcattgcc    1500
gaagtggaaa atgatgagat gcctgctgac ttgccttcat tagctgctga ttttgttgaa   1560
agtaaggatg tttgcaaaaa ctatgctgag gcaaaggatg tcttcctggg catgtttttg    1620
tatgaatatg caagaaggca tcctgattac tctgtcgtgc tgctgctgag acttgccaag    1680
acatatgaaa ccactctaga gaagtgctgt gccgctgcag atcctcatga atgctatgcc    1740
aaagtgttcg atgaatttaa acctcttgtg gaagagcctc agaattaat caaacaaat     1800 tgtgagcttt ttgagcagct tggagagtac aaattccaga atgcgctatt agttcgttac    1860
accaagaaag taccccaagt gtcaactcca actcttgtag aggtctcaag aaacctagga    1920
aaagtgggca gcaaatgttg taaacatcct gaagcaaaaa gaatgccctg tgcagaagac    1980
tatctatccg tggtcctgaa ccagttatgt gtgttcatg agaaaacgcc agtaagtgac     2040
agagtcacca aatgctgcac agaatccttg gtgaacaggc gaccatgctt ttcagctctg    2100
gaagtcgatg aaacatacgt tcccaaagag tttaatgctg aaacattcac cttccatgca    2160
gatatatgca cactttctga aaggagagaa caaatcaaga acaaactgc acttgttgag    2220 ctcgtgaaac acaagcccaa ggcaacaaaa gagcaactga agctgttat ggatgatttc     2280 gcagcttttg tagagaagtg ctgcaaggct gacgataagg agacctgctt tgccgaggag    2340
ggtaaaaaac ttgttgctgc aagtcaagct gccttaggct tataa                   2385
```

<210> SEQ ID NO 7
<211> LENGTH: 48
<212> TYPE: DNA
<213> ORGANISM: Artificial Sequence

```
<220> FEATURE:
<223> OTHER INFORMATION: Primer T62F

<400> SEQUENCE: 7
ctctggctcc ccggggcgcg ctgtttgcac tgccctgccg cctgtacc            48

<210> SEQ ID NO 8
<211> LENGTH: 45
<212> TYPE: DNA
<213> ORGANISM: Artificial Sequence
<220> FEATURE:
<223> OTHER INFORMATION: Primer T62R

<400> SEQUENCE: 8
gcaacctcac tcttgtgtgc atctgaacaa cggaatttct tgctt               45

<210> SEQ ID NO 9
<211> LENGTH: 23
<212> TYPE: DNA
<213> ORGANISM: Artificial Sequence
<220> FEATURE:
<223> OTHER INFORMATION: Primer T60F3

<400> SEQUENCE: 9
gatgcacaca agagtgaggt tgc                                       23

<210> SEQ ID NO 10
<211> LENGTH: 46
<212> TYPE: DNA
<213> ORGANISM: Artificial Sequence
<220> FEATURE:
<223> OTHER INFORMATION: Primer T59R

<400> SEQUENCE: 10
tggctgatta atgatcaatg aattcttata agcctaaggc agcttg              46
```